United States Patent
Nowak

(12) United States Patent (10) Patent No.: US 7,704,303 B2
Nowak (45) Date of Patent: Apr. 27, 2010

(54) FILTER FOR ABSORBING ODORIFEROUS MATTER FROM AMBIENT AIR

(75) Inventor: Steven J. Nowak, Richmond, VA (US)

(73) Assignee: Hamilton Beach Brands, Inc., Glen Allen, VA (US)

( * ) Notice: Subject to any disclaimer, the term of this patent is extended or adjusted under 35 U.S.C. 154(b) by 1160 days.

(21) Appl. No.: 11/315,876

(22) Filed: Dec. 22, 2005

(65) Prior Publication Data
US 2007/0144128 A1 Jun. 28, 2007

(51) Int. Cl.
*B01D 46/00* (2006.01)
(52) U.S. Cl. ............................. 96/108; 55/471; 55/484; 55/496; 96/121
(58) Field of Classification Search .................. 96/108, 96/121; 55/512–519, 482–484, 467, 471, 55/472, 496
See application file for complete search history.

(56) References Cited

U.S. PATENT DOCUMENTS

| | | | | |
|---|---|---|---|---|
| 3,343,682 A | * | 9/1967 | Harvith | ....................... 210/477 |
| 3,807,082 A | | 4/1974 | Hautmann et al. | |
| 5,087,276 A | * | 2/1992 | Snyder | ......................... 55/496 |
| 5,192,571 A | * | 3/1993 | Levy | ........................... 426/433 |
| 5,681,630 A | * | 10/1997 | Smick et al. | ............... 428/40.1 |
| 5,863,471 A | | 1/1999 | Stanek | |
| 6,398,127 B1 | | 6/2002 | Wingo | |
| 6,425,932 B1 | | 7/2002 | Huehn et al. | |
| 6,461,396 B1 | | 10/2002 | Barker et al. | |
| 6,610,118 B2 | | 8/2003 | Bryce et al. | |
| 6,686,760 B2 | | 2/2004 | Hirt | |
| 2003/0010001 A1 | | 1/2003 | Bryce et al. | |
| 2003/0126844 A1 | | 7/2003 | Huehn et al. | |
| 2003/0159415 A1 | | 8/2003 | Parket | |
| 2004/0168416 A1 | | 9/2004 | Huehn et al. | |

* cited by examiner

*Primary Examiner*—Duane Smith
*Assistant Examiner*—Ives Wu
(74) *Attorney, Agent, or Firm*—Panitch Schwarze Belisario & Nadel LLP

(57) ABSTRACT

A filter for absorbing odoriferous matter from ambient air has a single body with a line of weakness that extends across at least a portion of the body and divides the filter element into at least two separately usable sub-filters. The line of weakness permits the separation of the single filter element into the sub-filters without the use of a tool. The filter element can be used in combination with varying size air purification units. The filter element can be placed in the filter housing of a large air purifier or after separation the sub-filters can be used in multiple correspondingly sized smaller air purifiers.

9 Claims, 3 Drawing Sheets

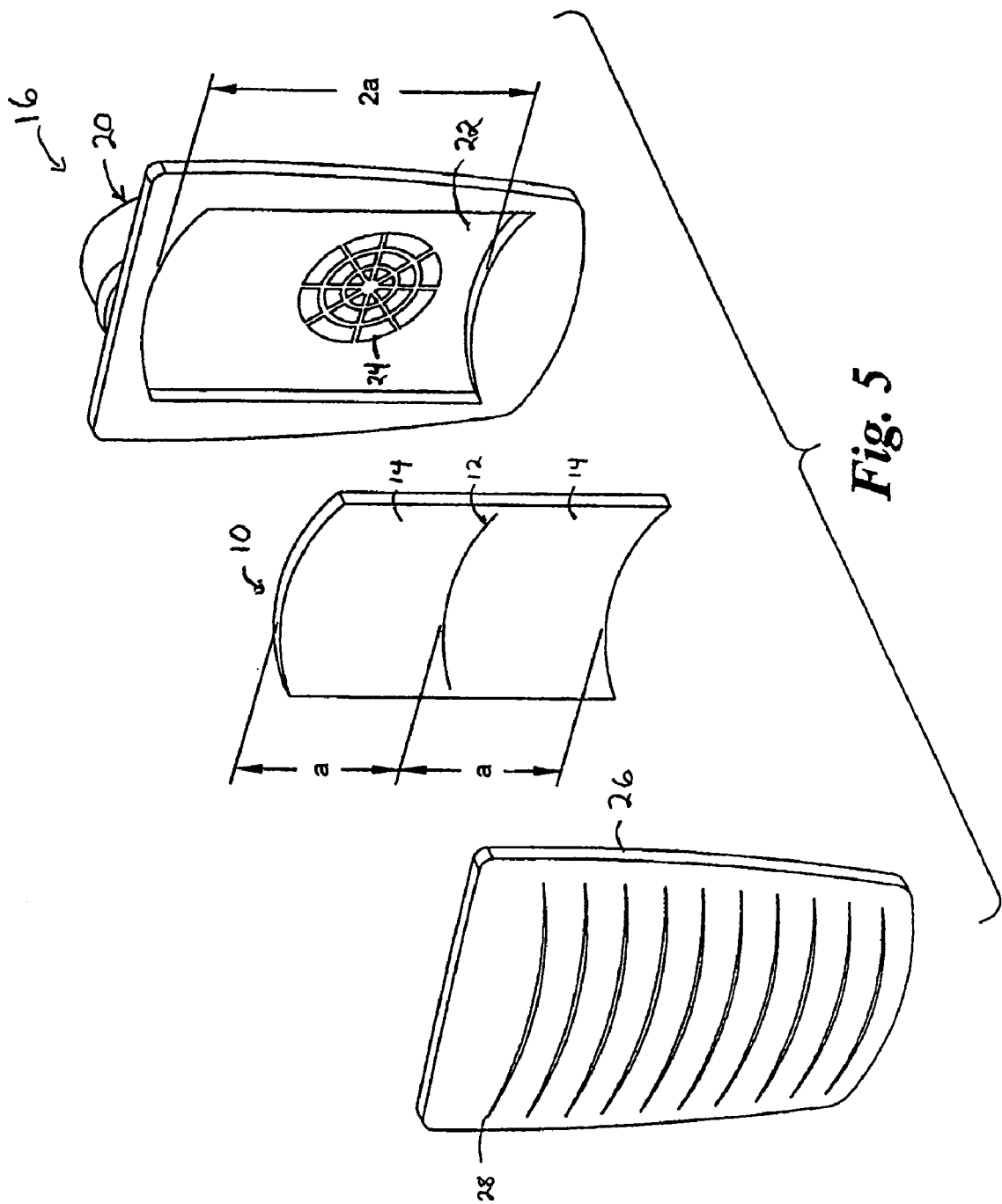

FILTER FOR ABSORBING ODORIFEROUS MATTER FROM AMBIENT AIR

BACKGROUND OF THE INVENTION

The present invention relates to air filters and, more particularly to a filter for absorbing odoriferous matter from ambient air.

Conventional air filters are common in the air purification art for absorbing odors. A typical filter is often manufactured for use in a specific air purifier. Since air purifiers come in different sizes, multiple filters must be manufactured and purchased to accommodate the varying sizes of the filters in the air purifiers on the market. Some attempts have been made to make more versatile filters, however such designs are inefficient and/or complex.

Prior art filters which have been developed for use in one larger filter housing maybe adjusted to fit a smaller filter housing, however none have been developed that can be used in a larger filter housing or multiple smaller filter housings. Current attempts at versatile filters are often complex, one requires a sliding saw tooth rack design, similar to window blinds. Other filter assemblies have been developed for combining smaller filters together by the frames, creating a filter to fit a larger sized filter housing. Such combined filters require the use of frames and excess attachment features to combine the smaller filters together. Further prior art filters require destructively removing part of the filter to fit a smaller size filter housing. The removed sections are not functional and must be discarded. All of the prior air filters are less desirable because of their complexity and/or inefficiency.

It would be advantageous to develop an air filter that could be placed in the housing of a large air filter or multiple smaller filters quickly and by hand. A simpler design could also reduce productions costs. It would be further desirable to develop a filter that is versatile between smaller and larger sized filter cavities and easily used. Currently filter manufacturers and dealers must carry larger inventories to service the requirements of different air purifiers. It would be further desirable to have a filter that can accommodate multiples sizes and reduce the number of filters manufacturers and dealers must have available.

SUMMARY OF THE INVENTION

Briefly stated, the present invention comprises a filter for absorbing odoriferous matter from ambient air. The filter is formed of a filter element of a single body and a line of weakness that extends across at least a portion of the body. The line of weakness divides the filter element into at least two separately usable sub-filters, without the use of a tool. The filter can be used in combination with a first air purifier having a filter housing of a first size or the sub-filters, can be used in a combination with a second air purifier having a smaller filter housing of a second size.

BRIEF DESCRIPTION OF THE SEVERAL VIEWS OF THE DRAWINGS

The foregoing summary as well as the following detailed description of a preferred embodiment of the present invention will be better understood when read in conjunction with the appended drawings. For the purpose of illustrating the invention, there is shown in the drawings an embodiment which is presently preferred. It is understood, however, the invention is not limited to the precise arrangements and instrumentalities shown. In the drawings:

FIG. 5 is an exploded perspective view of the filter element of FIG. 1 being used in combination with a air purifier of a first size.

DETAILED DESCRIPTION OF THE INVENTION

Figure 4:
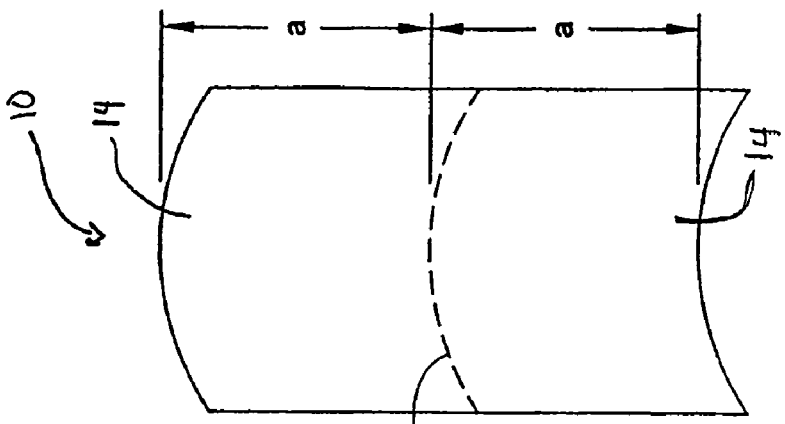
FIG. 4 is a front elevational view of a filter element for absorbing odoriferous matter from ambient air with a perforated line of weakness in accordance with a second preferred embodiment of the present invention.

Certain terminology is used in the following description for convenience only and is not limiting. The words "right," "left," "lower" and "upper" designate directions in the drawings to which reference is made. The words "inwardly" "and outwardly" refer to directions toward and away from, respectively, the geometric center of a filter element and designated parts thereof. The terminology includes the words above specifically mentioned, derivatives thereof and words of similar import. Additionally, the word "a" as used in the specification means at least one.

Figure 3:
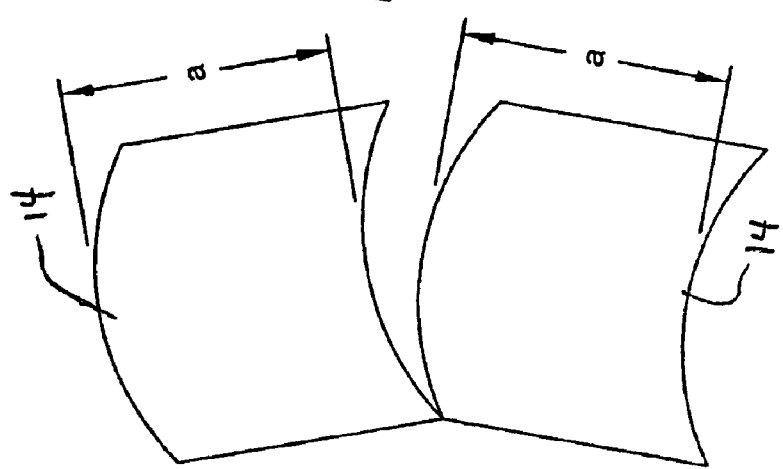
FIG. 3 is a front elevational view of the filter element of FIG. 1, being separated along the line of weakness into two separate sub-filters.
Figure 2:
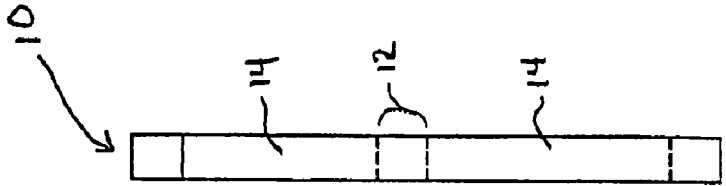
FIG. 2 is a side elevational view of the filter element of FIG. 1.
Figure 1:
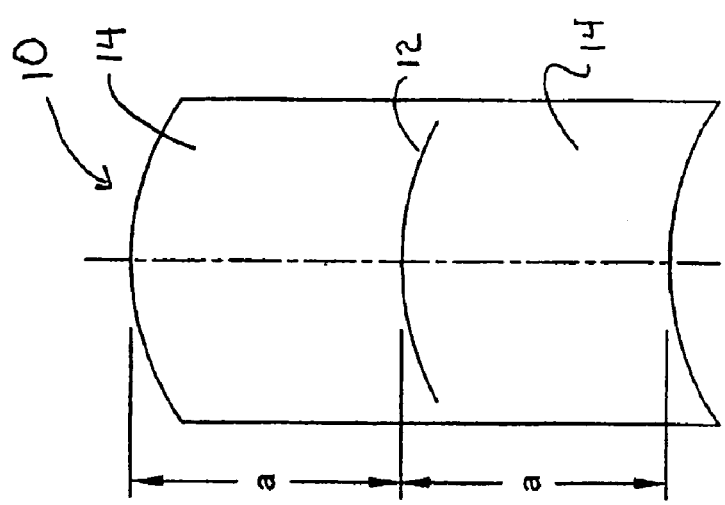
FIG. 1 is a front elevational view of a filter element for absorbing odoriferous matter from ambient air with a slit line of weakness in accordance with a first preferred embodiment of the invention.

Referring to the drawings in detail wherein like numerals indicate like elements throughout, there is shown in FIGS. 1-3 a first preferred embodiment of a filter element for absorbing odoriferous matter from ambient air, generally designated, 10. The filter element 10 has a line of weakness 12 extending across at least a portion of the body of the filter element 10 and divides the filter element 10 into separately usable sub-filters 14.

Figure 6:
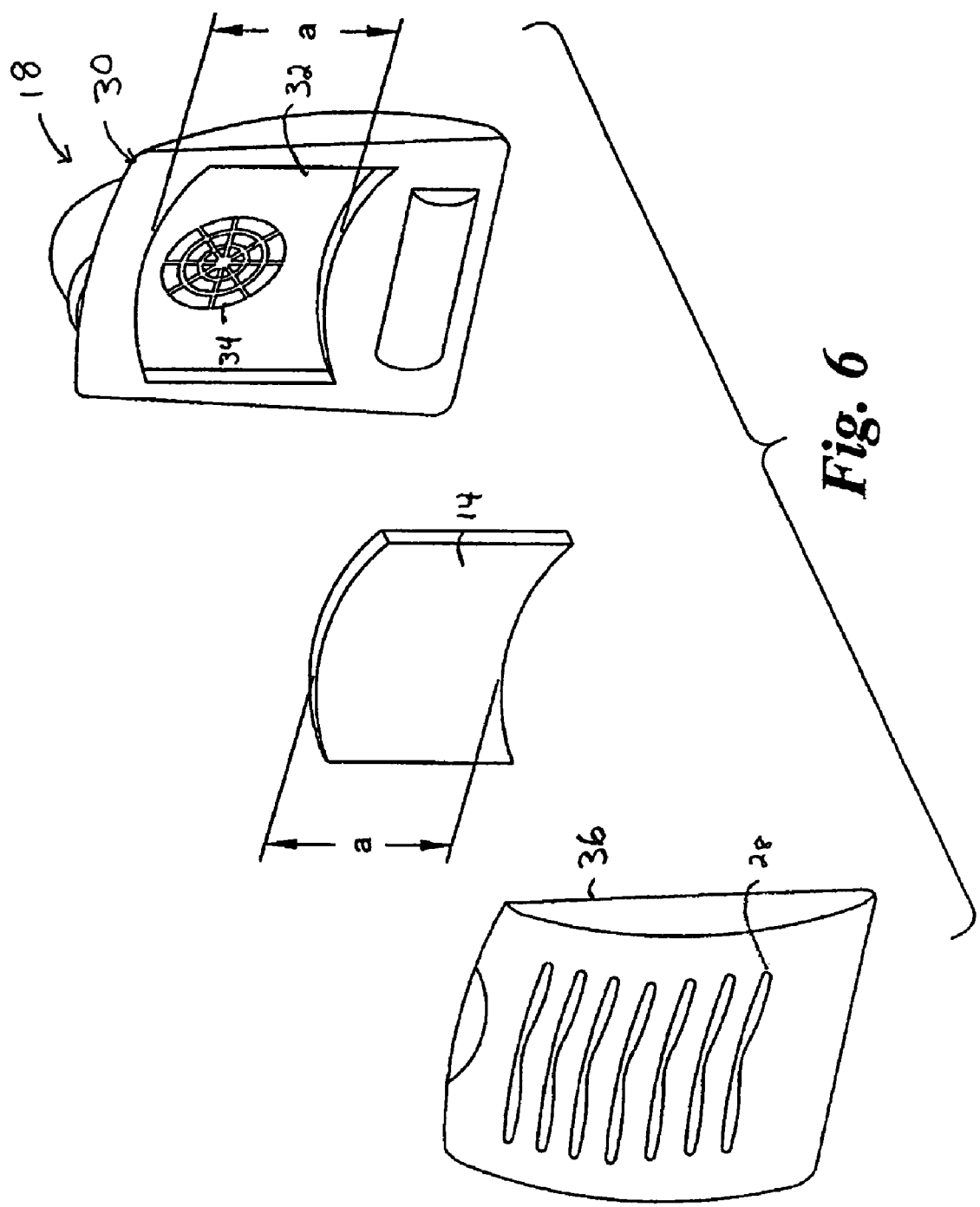
FIG. 6 is an exploded perspective view of a sub-filter being used in combination with an air purifier of a smaller second size.

The filter element 10 presently in the first preferred embodiment has a height of 5.43 inches (138 mm), a width of 3 inches (64 mm), a depth of 0.38 inches (10 mm) and a line of weakness 12 which is 2.53 inches (64 mm) down from the top of the filter element 10. The filter element 10 has a top and a bottom edge and a radius of 3.19 inches (81 mm). However it is understood the shape and dimension of the filter element 10 can be varied if desired, to suit particular applications. The line of weakness 12 is not restricted to a straight line, but instead could be any line, containing any number of curves. The design of the line of weakness 12 can be adjusted as needed so that the sub-filters 14, after separation, can fit into the filter housing 22, 32 of either a larger or smaller air purifier 16, 18, as shown in FIGS. 5 and 6.

The first preferred embodiment of the filter element 10 includes a porous structural matrix that holds at least one odor-absorbent chemical therein for circulation of ambient air there through. The porous structural matrix can be ten pores per inch (10 ppi) open cell foam coated with at minimum sixty (60) CTC carbon. It will be appreciated however by one skilled in the art that any commonly used filter material may be employed.

Referring to FIG. 1-4, the filter element 10 can be separated along the line of weakness 12 resulting in two equally sized sub-filters 14. The filter element 10 can be used without modification in a larger air purifier 16 or separated into the smaller sub-filters 14 for the use in two smaller air purifiers 18. The sub-filters 14 can both independently be used in separate air purifiers 18. The sub-filters 14 could also be used sequentially in the same air purifier 18, using a second sub-filter 14 to replace a worn out first sub-filter 14.

Referring to FIG. 1-3, in the first preferred embodiment the line of weakness 12 is a slit, extending across the majority of the middle of the front face of the filter element 10. The slit 12 runs partially across the front face of the filter element 10 so that the sub-filters 14 are connected by continuous filter material along and close to the side edges of the filter element 10. The slit 12 cuts through the full depth of the filter element 10 as shown in FIG. 3, and allows the filter element 10 to be easily separated by hand, by tearing through the material at both sides of the slit 12. Tearing along the slit 12 results in a clean separation and avoids jagged edges at the previously connected points along the sub-filters 14 by directing the applied separating forces.

Referring now to FIG. 4, in a second preferred embodiment, the line of weakness 12 is comprised of a perforation 12'. A user can tear the filter element 10 along the perforation 12' to separate the filter element 10 into the separate sub-filters 14. The perforation 12' extends across the entire front face of the filter element 10. It will be appreciated by a person skilled in the art that the line of weakness 12 is not limited to the above described slit 12 and perforation 12' and may be achieved by various alternative separation methods.

FIG. 5 is a perspective view of an air purifier 16 that can be used in connection with the described filter element 10. The air purifier 16 is comprised of four main sections, an air purifier housing 20, a filter housing 22, an air flow aperture 24 and a front cover plate 26. The air purifier housing 20 contains a motor, fan, controls and electrical source (not shown). The filter housing 22 is located in the front of the air purifier 20 housing and is shaped so that the filter element 10 can be tightly pressed into place and not shift laterally or vertically. The front cover plate 26 fits over the filter housing 22 and attaches to the air purifier housing 20. The front cover plate 26 contains a series of openings 28 through which air enters the air purifier 16. The ambient air is pulled by the fan in the filter housing 20 through the openings 28 in the front cover plate 26, through the filter element 10, and the air flow aperture 24 and then through the air purifier housing 20 and out an opening located therein. Air purifiers can be manufactured so the filter housing 22 is properly sized to fit the filter elements 10 before or after separation across the line of weakness 12 into sub-filters 14. The sub-filters 14 can then be used in the same manner described above in an air purifier 18 with a smaller sized filter housing 32 as visible in FIG. 6. It is understood by one skilled in the art that the described preferred embodiment is only an example of how the filter element 10 could be utilized.

As best shown in FIGS. 5-6, the combination use of the odor-absorptive filter element 10 in both a larger and smaller air purification unit 16, 18, similar to those described above. The filter element 10 before separation can be used independently to fit the filter housing 22 of the larger air purifier 16. After separation along the line of weakness 12, the two sub-filters 14 are both correctly sized to fit into the smaller sized filter housings 32. The air purifiers 16, 18 are both similarly configured having correspondingly scaled air purifier housings 20, 30, filter housings 22, 32, air flow apertures 24, 34 and front cover plates 26, 36. The versatility of the filter element 10 allows it to be a standard for both the larger and smaller sized air purification units 16,18.

From the foregoing description, it can be seen that the present invention comprises an improved filter element for absorbing odoriferous matter 10. It will be appreciated by those skilled in the art that changes could be made to the embodiment described in the forgoing description without departing from the broad inventive concepts thereof. It is understood, therefore, that the invention is not limited to the particular embodiments disclosed, but is intended to cover all modifications which are within the scope and spirit of the invention as defined by the appended claims.

I claim:

1. A filter for absorbing odoriferous matter from ambient air, said filter comprising:

a filter element in the form of a single body and including a porous structural matrix holding at least one odor-absorbent chemical therein for circulation of air therethrough; and a line of weakness extending across at least a portion of the body dividing the filter element into at least two equally sized and separately usable sub-filters, each sub-filter being independently usable in separate air purifiers, the line of weakness allowing the separation of the single body into the sub-filters without the use of a tool.

2. The filter of claim 1, wherein the line of weakness is a generally straight slit extending from a first end to an opposing second end of the single body and through a geometric center of the single body.

3. The filter of claim 1, wherein the line of weakness is formed by a series of perforations.

4. An air purifier having an air purifier housing, a filter housing, an air flow aperture, a front cover plate and a filter for absorbing odoriferous matter from ambient air, the filter housing being located in a front portion of the air purifier housing and being shaped to tightly accommodate the filter to prevent lateral or vertical shifting thereof, said filter comprising:

a filter element in the form of a single body; and a line of weakness extending across at least a portion of the body dividing the filter element into at least two equally sized and separately usable sub-filters, each sub-filter being independently usable in separate air purifiers, the line of weakness allowing the separation of the single body into the sub-filters without the use of a tool.

5. A combination odor-absorptive filter and varying size air purification units, the combination comprising: a first air purifier having a first filter housing of a first size; a second air purifier having a second filter housing of a second size, the second size being smaller than the first size; and a filter element in the form of single body; a line of weakness extending across at least a portion of the body dividing the filter element into at least two separately usable sub-filters, the line of weakness allowing the separation of the single body into the sub-filters without the use of a tool, the filter element in the form of a single body being correspondingly sized to fit in the first filter housing, the two sub-filters being correspondingly sized to fit in the second filter housing, whereby a user can use the filter element in the form of a single body in the first air purifier or can separate the single body into two sub-filters for use in the second air purifier.

6. The combination of claim 5, wherein the filter element comprises a porous structural matrix holding at least one odor-absorbent chemical therein for circulation of air therethrough.

7. The combination of claim 5, wherein the line of weakness is a slit extending across a majority of a middle portion of the filter element.

8. The combination of claim 5, wherein the line of weakness is formed by a series of perforations.

9. The filter of claim 5, wherein the line of weakness generally divides the single body into at least two equal sized sub-filters.

* * * * *